(12) United States Patent
Lee

(10) Patent No.: US 9,314,645 B1
(45) Date of Patent: Apr. 19, 2016

(54) OPTICAL FIBER FOR PRODUCING HEAT AND METHOD FOR MANUFACTURING THE SAME

(71) Applicant: DIOTECH CO., LTD., Busan (KR)

(72) Inventor: Kyung Yong Lee, Busan (KR)

(73) Assignee: DIOTECH CO., LTD., Busan (KR)

( * ) Notice: Subject to any disclaimer, the term of this patent is extended or adjusted under 35 U.S.C. 154(b) by 0 days.

(21) Appl. No.: 14/553,525

(22) Filed: Nov. 25, 2014

(30) Foreign Application Priority Data

Nov. 24, 2014 (KR) .......................... 10-2014-0164471

(51) Int. Cl.
G02B 6/26 (2006.01)
G02B 6/42 (2006.01)
A61N 5/06 (2006.01)
G02B 6/24 (2006.01)
G02B 6/122 (2006.01)
A61N 5/067 (2006.01)
G02B 6/44 (2006.01)

(52) U.S. Cl.
CPC ............ *A61N 5/0625* (2013.01); *G02B 6/1228* (2013.01); *G02B 6/241* (2013.01); *G02B 6/262* (2013.01); *A61N 2005/0602* (2013.01); *A61N 2005/063* (2013.01); *A61N 2005/067* (2013.01); *G02B 6/4488* (2013.01)

(58) Field of Classification Search
CPC ...... G02B 6/1228; G02B 6/241; G02B 6/262; G02B 6/4488; A61N 5/0625; A61N 2005/063; A61N 2005/0602; A61N 2005/067
See application file for complete search history.

(56) References Cited

U.S. PATENT DOCUMENTS

| | | | |
|---|---|---|---|
| 2008/0188843 A1* | 8/2008 | Appling ................. | A61B 18/24 606/15 |
| 2008/0215041 A1* | 9/2008 | Zemmouri ............. | A61B 18/22 606/15 |
| 2009/0240242 A1* | 9/2009 | Neuberger ............. | A61B 18/24 606/7 |
| 2011/0282330 A1* | 11/2011 | Harschack ............. | A61B 18/24 606/3 |
| 2015/0057648 A1* | 2/2015 | Swift .................... | A61B 18/245 606/15 |

FOREIGN PATENT DOCUMENTS

KR      20-0461454 Y1      7/2012

* cited by examiner

*Primary Examiner* — Ryan Lepisto
(74) *Attorney, Agent, or Firm* — Novick, Kim & Lee, PLLC; Jae Youn Kim

(57) ABSTRACT

Provided is an optical fiber for producing heat wherein a reflection tube (13) is wrapped on its outer peripheral surface by a heat conduction tube (14) to block laser beam from being irradiated outside, and a plurality of grooves are formed on a side of an optical fiber (11) so as to transmit laser beam to the side of the optical fiber (11) at 360° around a central axis of the optical fiber (11) where a cloth (12) is peeled away such that the area where heat is produced is expanded to a whole length direction of the optical fiber (11) where the cloth (12) is peeled away between the optical fiber (11) and the reflection tube (13).

7 Claims, 2 Drawing Sheets

OPTICAL FIBER FOR PRODUCING HEAT AND METHOD FOR MANUFACTURING THE SAME

CROSS-REFERENCE(S) TO RELATED APPLICATION

This application claims priority of Korean Patent Application No. 10-2014-0164471, filed on Nov. 24, 2014, in the Korean Intellectual Property Office, which is hereby incorporated by reference in its entirety.

BACKGROUND OF THE INVENTION

1. Field of the Invention

The present invention relates to an optical fiber for producing heat and a method for manufacturing the same, and more particularly, to an optical fiber for producing heat and a method for manufacturing the same which aims at contracting blood vessel smoothly with heat produced uniformly by using laser beam passing through optical fiber, not using high frequency, so as to contract blood vessel by producing heat within the blood vessel to treat varicose vein.

2. Description of the Related Art

In general, referring to contracting blood vessel by applying heat thereto, there has been two ways, one is using high frequency and the other is using irritation of laser beam.

Meanwhile, optical fiber is used for irradiating laser beam wherein mostly the laser beam is irradiated into blood vessel through a remote end of the optical fiber and a reflection tube to contract the blood vessel.

However, in this case laser energy is produced excessively to damage blood vessel and further optical fiber contacts directly a blood vessel wall to perforate the blood vessel.

Accordingly, a study is needed in the related technical field for preventing the blood vessel damage and perforation of the blood vessel by being direct contact with optical fiber, thereby performing stably surgical operation.

SUMMARY OF THE INVENTION

The present invention has been proposed to solve the above drawbacks and one object of the present invention is to provide an optical fiber for producing heat and a method for manufacturing the same, in which referring to a way for producing heat by irradiating laser beam into blood vessel through an optical fiber, the laser beam is not irradiated directly into blood vessel but produce only heat so as to overcome problems caused from the way for later beam itself gives energy to blood vessel or blood as an energy source so that the inside of blood vessel is kept at a preset temperature to remove the side effects caused from laser beam having excessive energy and obtain the same surgical effects as high frequency.

An aspect of the present invention is directed to an optical fiber for producing heat wherein a reflection tube (13) may be wrapped on its outer peripheral surface by a heat conduction tube (14) to block laser beam from being irradiated outside, and a plurality of grooves may be formed on a side of an optical fiber (11) so as to transmit laser beam to the side of the optical fiber (11) at 360° around a central axis of the optical fiber (11) where a cloth (12) is peeled away such that the area where heat is produced is expanded to a whole length direction of the optical fiber (11) where the cloth (12) is peeled away between the optical fiber (11) and the reflection tube (13).

At this time, the reflection tube (13) may be made of one of glass, reinforced glass, Pyrex, sapphire, ceramic, and acryl.

Further, the heat conduction tube (14) may be made of one of stainless steel, tungsten, titanium, aluminum, aluminum alloy, copper, bronze, bronze alloy, cast iron, other metals, and nonmetallic material.

Another aspect of the present invention is directed to a method for manufacturing an optical fiber for producing heat, including: a first step of forming two or more of one of reflection type grooves and circular grooves in a conical shape with respect to a side of an optical fiber by processing precisely a side of the optical fiber (11) while peeling away a cloth (12) at one side of the optical fiber (11) and adjusting a horizontal angle around a central axis of the optical fiber (11), or processing at least two or more by combining each groove; and a second step of enveloping the optical fiber (11) where the cloth (12) is peeled away with the reflection tube (13) and then wrapping additionally the outside of the reflection tube (13) with a heat conduction tube (14) thereby to block laser beam from being irradiated outside and produce heat within the reflection tube (13), and boding the reflection tube (13) and the heat conduction tube (14) so as to prevent the reflection tube (13) from be detached.

At this time, the first step may include forming sequentially a second circular groove (11d), a first circular groove (11c), a second reflection type groove (11b), and a first reflection type groove (11a) to be spaced each other between a rear end of a remote end (11e) of the optical fiber (11) and a front end of the cloth (12).

Further another aspect of the present invention is directed to an optical fiber for producing heat wherein at least one of a reflection tube (13) and a heat conduction tube (14) is wrapped so as to prevent laser beam transmitted through an optical fiber (11) from being irradiated outside and a plurality of grooves are formed on a side of the optical fiber (11) so as to transmit laser beam to the side of the optical fiber (11) at 360° around a central axis of the optical fiber (11) where a cloth (12) is peeled away such that the area where heat is produced is expanded to a whole length direction of the optical fiber (11) where the cloth (12) is peeled away between the optical fiber (11) and the reflection tube (13).

BRIEF DESCRIPTION OF THE DRAWINGS

The above and other aspects, features and advantages of certain exemplary embodiments of the present invention will be more apparent from the following description taken in conjunction with the accompanying drawings, in which.

Figure 1:
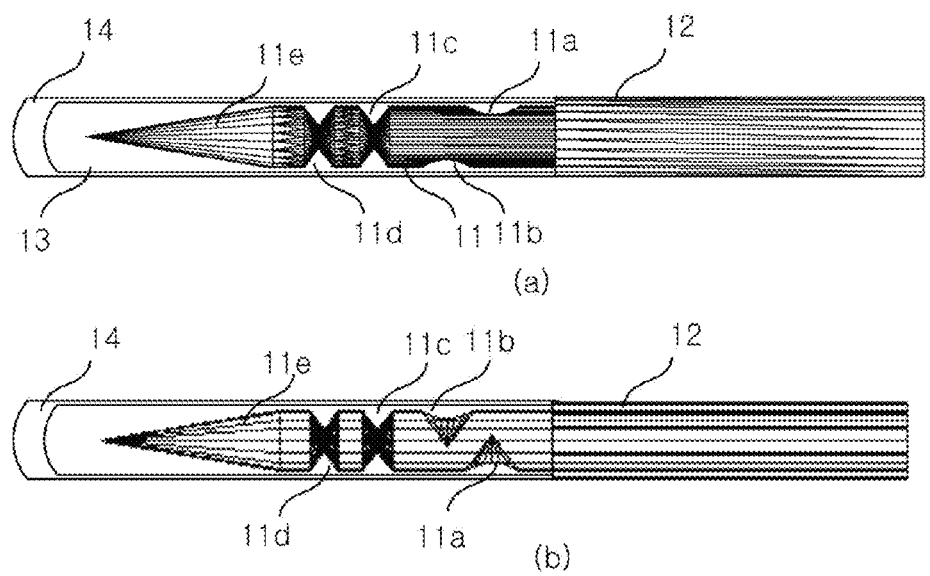
FIG. 1 is a side view illustrating schematically an optical fiber for producing heat according to an embodiment of the present invention.

It should be understood that the appended drawings are not necessarily to scale, presenting a somewhat simplified representation of various preferred features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION OF EXEMPLARY EMBODIMENTS

Exemplary embodiments of the present invention will be described below in detail with reference to the accompanying drawings. Wherever possible, the same reference numerals will be used to refer to the same elements throughout the specification, and a duplicated description thereof will be omitted. It will be understood that although the terms "first", "second", etc. are used herein to describe various elements, these elements should not be limited by these terms. These terms are only used to distinguish one element from another element.

Figure 2:
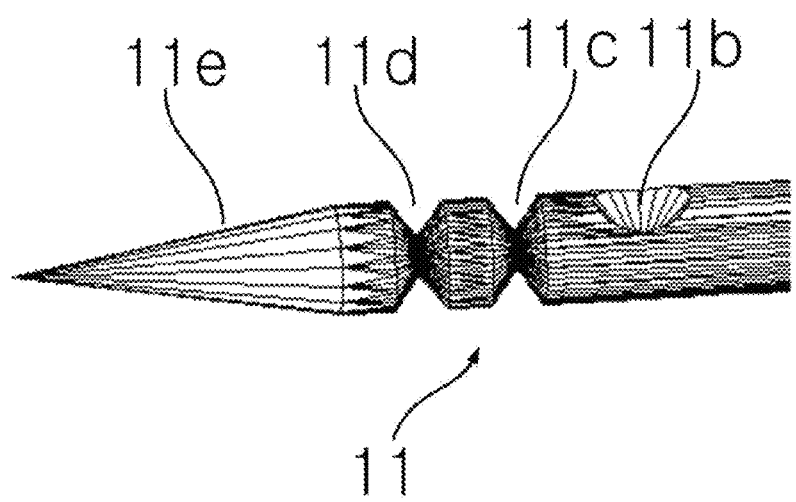
FIG. 2 is a perspective view illustrating in detail an optical fiber 11 among the optical fiber for producing heat as shown in FIG. 1.
Figure 3:
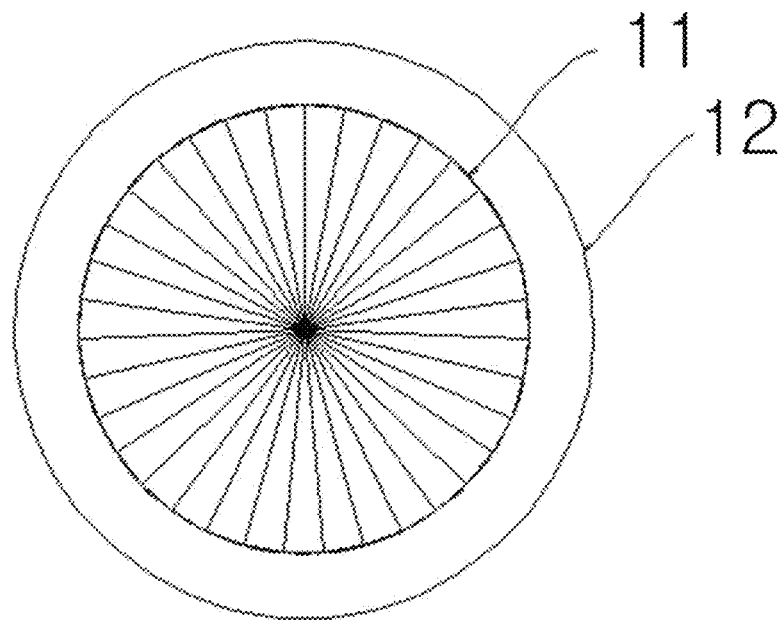
FIG. 3 is a front view illustrating the optical fiber for producing heat as shown in FIG. 1.
Figure 4:
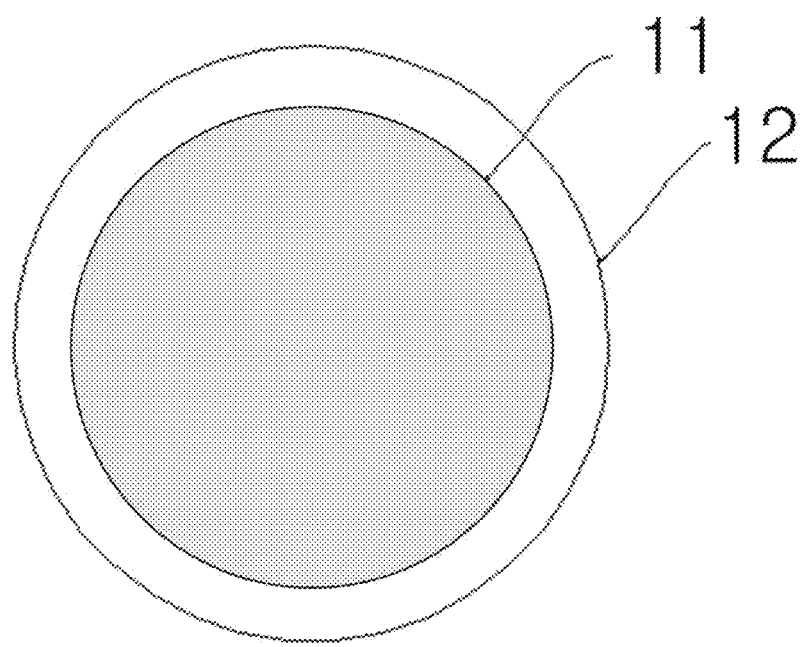
FIG. 4 is a rear view illustrating the optical fiber for producing heat as shown in FIG. 1.

FIG. 1 is a side view illustrating schematically an optical fiber for producing heat according to an embodiment of the present invention, FIG. 2 is a perspective view illustrating in detail an optical fiber 11 among the optical fiber for producing heat as shown in FIG. 1, FIG. 3 is a front view illustrating the optical fiber for producing heat as shown in FIG. 1, and FIG. 4 is a rear view illustrating the optical fiber for producing heat as shown in FIG. 1.

Referring to FIGS. 1 to 4, the optical fiber for producing heat according to an embodiment of the present invention is provided with an optical fiber 11 and a cloth 12, which are arranged sequentially from inner side to outer side around a concentric circle, and a reflection tube 13 and a heat conduction tube 14 where the cloth 12 is peeled away among the optical fiber 11. Meanwhile, the reflection tube 13 and the heart conduction tube 14 may be disposed variously.

The optical fiber 11, as shown in FIG. 1, a first reflection type groove 11a, a second reflection type groove 11b, a first circular groove 11c, a second circular groove 11d and a remote end lie of the optical fiber.

In more detail, the optical fiber 11 is configured by the reflection type grooves and the circular grooves for producing heat, which are formed on a side of the optical fiber 11, the thin and long remote end lie, the reflection tube 13 that wraps whole area corresponding to a side of the optical fiber 11 and a heat conduction tube 14 that covers whole outer peripheral surface thereof.

The laser beam is reflected continuously through the reflection tube 13 of a fixing substance to produce heat while the laser beam transmitted through the optical fiber 11 is not irradiated outside the heat conduction tube 14 corresponding to an outer wall of the reflection tube 13 of a fixing substance so that the produced heat is transmitted into blood vessel while the produced heat is maintained within a preset temperature range.

Here, the reflection tube 13 may be made of glass, reinforced glass, Pyrex, sapphire, ceramic, acryl or the like, and the reflection tube serves to maintain heat at a constant level by reflecting and refracting continuously heat in a length direction when laser beam is irradiated through the optical fiber 11.

As a result, the laser beam that is irradiated using an optical fiber produces heat at the first reflection type groove 11a, the second reflection type groove 11b, the first circular groove 11c, the second circular groove 11d and an inner space of the reflection tube 13 along a whole length of the reflection tube 13, not at one place of the remote end of the optical fiber as in a related art, thereby transmitting the heat into blood vessel.

As shown in FIGS. 1 and 2, the second circular groove 11d, the first circular groove 11c, the second reflection type groove 11b and the first reflection type groove 11a are formed sequentially to be space each other between a rear end of the remote end 11e among the optical fiber 11 and a front end of the cloth 12 so that laser beam is irradiated to multi-directions.

Eventually, the heat is produced by the laser beam that is transmitted through the optical fiber 11 evenly at a side of the reflection tube 13 a section of which is a cylinder shape and at a front of the reflection tube a section of which is hemispheric.

Even though side effects are produced when irradiating laser to blood vessel to treat varicose vein according to a related art, the optical fiber for producing heat configured as described above according to the present invention does not irradiate directly laser beam into blood vessel of a human body but transmit heat thereto thereby to serve heat operation like high frequency to perform stably surgical operation.

Further, the heat within the reflection tube 13 is maintained at a constant level using the first reflection type groove 11a, the second reflection type groove 11b, the first circular groove 11c, the second circular groove 11d so that the side effects caused from excessive laser can be prevented.

When manufacturing the optical fiber for producing heat, a cloth 12 at one side of an optical fiber 11 is peeled away and the side of the optical fiber 11 is processed precisely while adjusting a horizontal angle around a central axis of the optical fiber 11 to form two or more of reflection grooves and circular grooves in a conical form, or at least two are processed by combining the reflection grooves and the circular grooves.

Meanwhile, it is shown in FIGS. 1 and 2 that the first circular groove 11c and the second circular groove 11d are processed additionally in addition to the first reflection type groove 11a and the second reflection type groove 11b, however, the first circular groove 11c and the second circular groove 11d may be replaced with the reflection type grooves such that the reflection grooves are disposed at equal angle around 360 degree of clockwise or counter-clockwise. On the contrary, the first reflection type groove 11a and the second reflection type groove 11b may be replaced with the circular grooves.

After processing precisely the optical fiber 11, the optical fiber 11 of which the cloth 12 is peeled away is enveloped by a reflection tube 13 and then the outside of the reflection tube 13 is wrapped by a heat conduction tube 14 to block laser beam from being irradiated outside thereby to produce heat within the reflection tube 13. Here, the reflection tube 13 and the heat conduction tube 14 are bonded to prevent the reflection tube 13 from being detached.

The reflection tube 13 may be made of glass and the heat conduction tube 14 may be made of stainless, however, there is no limitation thereof, and thus the reflection tube 13 may be made of any materials having properties of transmission, reflection and refraction of light including laser beam and the stainless of the heat conduction tube 14 may be replaced with material of light block and heat conductive. In more detail, the reflection tube 13 is made mainly of glass, however, the reflection tube may be made of glass, reinforced glass, Pyrex, sapphire, ceramic, acryl or the like, and the heat conduction tube 14 may be made of stainless steel, tungsten, titanium, aluminum, aluminum alloy, copper, bronze, bronze alloy, cast iron or other metals, or nonmetallic material. Meanwhile, the reflection tube 13 may be made of transparent material, semitransparent material or opaque material through which channels are formed.

That is, an outer peripheral surface of the reflection tube 13 is wrapped by the heat conduction tube 14 to block the laser beam that is transmitted through the optical fiber 11 from being irradiated outside and a plurality of reflection type grooves or circular grooves are formed on a side of the optical fiber 11 where the cloth 12 is peeled away so as to transfer laser beam so that the heat is produced evenly by the laser beam along a length direction of the heat conduction tube 14 outside the reflection tube 13.

Meanwhile, a diameter of the optical fiber may be from 0.1 mm to 100 mm, and frequency for transferring laser beam may be from 400 nm to 20000 nm and a length of the optical fiber 11 may be from 1 cm to 1000 cm.

Further, a total length of the reflection tube 13 and the heat conduction tube 14 may be from 1 mm to 500 mm, a diameter, inner diameter and outer diameter thereof may be from 0.001 mm to 1000 mm wherein a diameter of the reflection tube 13 is shorter than that of the heat conduction tube 14, as shown in FIG. 1.

As an modified embodiment of the present invention, a section of the reflection tube 13 or the heat conduction tube 14 may be an oval shape, triangular shape or quadrangular shape in addition to a circular shape, and a shape of the remote end thereof may be a conical shape, a concave shape, triangular shape, quadrangular shape or digon shape at spherical geometrics in addition to hemispheric shape.

Meanwhile, a boding surface of the reflection tube 13, the heat conduction tube and the cloth 12 may be blocked or opened.

According to an optical fiber for producing heat and a method for manufacturing the same, the optical fiber does not irradiate laser beam into blood vessel but transmit the laser beam thereto and serves as heat operation like high frequency so as to treat varicose vein, thereby improving side effects caused from irradiating directly into blood vessel according to a related art and performing stably surgical operation.

Further, according to an optical fiber for producing heat and a method for manufacturing the same a whole temperature outside the heat conduction tube is kept at a constant level through each of reflection type grooves or circular grooves or a combination thereof, thereby preventing side effects caused from excessive laser.

While the invention has been shown and described with reference to exemplary embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present invention.

What is claimed is:

1. An optical fiber assembly for producing heat, comprising:
    an optical fiber;
    a reflection tube wrapped on an outer peripheral surface of the optical fiber by a heat conduction tube to block laser beam from being irradiated outside; and
    a plurality of grooves disposed on a side of the optical fiber so as to transmit laser beam to the side of the optical fiber at 360° around a central axis of the optical fiber,
    wherein a cloth is peeled away such that an area where heat is produced is expanded to a whole length direction of the optical fiber where the cloth is peeled away between the optical fiber and the reflection tube.

2. The optical fiber assembly for producing heat of claim 1, wherein the reflection tube is made of one of glass, reinforced glass, Pyrex, sapphire, ceramic, and acryl.

3. The optical fiber assembly for producing heat of claim 1, wherein the heat conduction tube is made of one of stainless steel, tungsten, titanium, aluminum, aluminum alloy, copper, bronze, bronze alloy, cast iron, other metals, and nonmetallic material.

4. A method for manufacturing an optical fiber assembly for producing heat, comprising:
    a first step of forming two or more reflection type grooves or two or more circular grooves, or forming in combination two or more grooves of the reflection type grooves and the circular grooves in a conical shape with respect to a side of an optical fiber by processing precisely the side of the optical fiber while peeling away a cloth at one side of the optical fiber and adjusting a horizontal angle around a central axis of the optical fiber; and
    a second step of enveloping the optical fiber where the cloth is peeled away with the reflection tube and then wrapping additionally an outside of the reflection tube with a heat conduction tube thereby to block laser beam from being irradiated outside and produce heat within the reflection tube, and bonding the reflection tube and the heat conduction tube so as to prevent the reflection tube from being detached.

5. The method for manufacturing an optical fiber assembly for producing heat of claim 4, wherein the first step comprises forming sequentially a second circular groove, a first circular groove, a second reflection type groove, and a first reflection type groove to be spaced each other between a rear end of a remote end of the optical fiber and a front end of the cloth.

6. An optical fiber assembly for producing heat, comprising:
    an optical fiber;
    at least one of a reflection tube and a heat conduction tube wrapped so as to prevent laser beam transmitted through the optical fiber from being irradiated outside; and
    a plurality of grooves disposed on a side of the optical fiber so as to transmit laser beam to the side of the optical fiber at 360° around a central axis of the optical fiber,
    wherein a cloth is peeled away such that an area where heat is produced is expanded to a whole length direction of the optical fiber where the cloth is peeled away between the optical fiber and the reflection tube.

7. The optical fiber assembly for producing heat of claim 6, wherein the reflection tube and the heat conduction tube are disposed in a switching manner.

* * * * *